United States Patent [19]
Karp et al.

[11] Patent Number: 6,154,727
[45] Date of Patent: Nov. 28, 2000

[54] VISIT VERIFICATION

[75] Inventors: Edward W. Karp; Kevin J. Bianchini; David R. Fine, all of New Orleans, La.; Jonathan M. Fine, Weston, Conn.; Cedric F. Walker, New Orleans, La.

[73] Assignee: CyberHealth, Inc., New Orleans, La.

[21] Appl. No.: 09/060,855

[22] Filed: Apr. 15, 1998

[51] Int. Cl.⁷ .................................................. G06F 17/60
[52] U.S. Cl. ...................... 705/3; 705/2; 705/9; 455/456; 455/404; 455/457
[58] Field of Search .................................... 455/404, 410, 455/411, 456, 457; 705/2, 3, 1, 30, 9; 379/37, 38, 45, 127, 142, 247, 93.03, 88.02; 380/23

[56] References Cited

U.S. PATENT DOCUMENTS

| | | | |
|---|---|---|---|
| 5,109,399 | 4/1992 | Thompson | 379/45 |
| 5,208,756 | 5/1993 | Song | 455/456 |
| 5,218,367 | 6/1993 | Sheffer et al. | 455/456 |
| 5,255,183 | 10/1993 | Katz | 705/30 |
| 5,327,144 | 7/1994 | Stilp et al. | 455/456 |
| 5,479,482 | 12/1995 | Grimes | 455/457 |
| 5,515,419 | 5/1996 | Sheffer | 455/456 |
| 5,519,760 | 5/1996 | Borkowski et al. | 455/456 |
| 5,608,784 | 3/1997 | Miller | 379/127 |
| 5,646,839 | 7/1997 | Katz | 379/142 |
| 5,666,662 | 9/1997 | Shibuya | 455/456 |
| 5,732,354 | 3/1998 | MacDonald | 455/456 |
| 5,758,317 | 5/1998 | Peterson et al. | 704/247 |
| 5,815,538 | 9/1998 | Grell et al. | 455/456 |
| 5,815,814 | 9/1998 | Dennison et al. | 455/456 |
| 5,835,575 | 11/1998 | Stoller et al. | 379/38 |
| 5,844,522 | 12/1998 | Sheffer et al. | 455/456 |
| 5,862,223 | 1/1999 | Walker et al. | 705/1 |
| 5,873,040 | 2/1999 | Dunn et al. | 455/456 |
| 5,953,650 | 9/1999 | Villevieille | 455/404 |
| 5,960,337 | 9/1999 | Brewster et al. | 455/404 |
| 5,963,861 | 10/1999 | Hanson | 455/456 |
| 6,006,096 | 12/1999 | Trompower | 455/456 |
| 6,011,974 | 1/2000 | Cedarvall et al. | 455/456 |
| 6,049,718 | 4/2000 | Stewart | 455/456 |

FOREIGN PATENT DOCUMENTS

WO 97/17623  5/1997  WIPO.

OTHER PUBLICATIONS

Washington Times, "Secret Service, Cellular Firms Attack Fraud", Dialog File 635:Business Dateline, pp. 1–2, Apr. 1995.

PR Newswire, "T–NETIX Installs SpeakEZ Voice Print (SM) Solution For Intrust Bank", Dialog File 621:IAC New Product Announcement, pp. 1–2, Aug. 1997.

Primary Examiner—Emanuel Todd Voeltz
Assistant Examiner—John W. Hayes
Attorney, Agent, or Firm—Michael D. Carbo

[57] ABSTRACT

The invention relates to a system and method for tracking clients as they visit the locations of various recipients. Clients have access to telephones and identification devices which the client can use to communicate with a remote computer. The computer uses information received during the communication to identify and authenticate the client making the communication and the location of the client at the time of the communication. Authentication is accomplished by obtaining unique biometric parameters from a client over the phone and comparing those to biometric parameters in a database. Biometric data can include a voice print sampled during the call, or a finger or retinal print electronically transmitted during the call. Because each of these identifiers results from a physiological characteristic which is unique to the client, the system assures that the identified client is the client making the communication. The system can include logic for identifying the address of a cellular phone at the time a phone call is placed. The logic does not require an automatic number identification (ANI). In fact, the ANI of a cellular phone may not provide any location information because the phone itself is mobile. Instead the logic uses information provided by the cellular carrier to identify the origin of the call with regard to the cell stations receiving the call. Accordingly, the client can be tracked when the client is using a cellular phone to communicate with the computer.

9 Claims, 14 Drawing Sheets

PSTN CELLULAR PHONE DATABASE — 134C2

| Cell Identifier | Cell Address/Geographic Location |
|---|---|
| LU-23571-4B | 44 Okalobee St. |
| NY-83632-3C | 71.22.11-128.29.12 |
|  |  |
|  |  |
|  |  |
|  |  |
|  |  |

PSTN/STANDARD PHONE DATABASE — 134C1

| Phone Number | Subscriber Name | Address | Cellular/Fixed |
|---|---|---|---|
| 650 493-9300 | Wilson Sonsini.. | 2 Page Mill Rd. | Cellular |
| 415 949-3303 | Netherlands | 4400 Commerce | Fixed |
| 203 645-5200 | Patient 1 | 245 Fairmont | Fixed |
|  |  |  |  |
|  |  |  |  |
|  |  |  |  |
|  |  |  |  |

712 / 714 / 716 / 718

PSTN PARAMETERS

FIGURE 7A

| Caller/Client Name | Client Employee | Recipient Address | Recipient Name | Arrival Time | Departure Time | Time Spent with Recipient | Task Codes |
|---|---|---|---|---|---|---|---|
| 100A | WVA-1 | 245 Fairmont | Patient 1 | 12PM | 4PM | 4 hours | 245-236 |
| | | | | | | | |
| | | | | | | | |
| | | | | | | | |
| | | | | | | | |
| | | | | | | | |
| | | | | | | | |

REPORT

FIGURE 9

VISIT VERIFICATION

BACKGROUND OF THE INVENTION

1. Field of Invention

The invention relates to a system and method for tracking the activity of caller/clients visiting recipients, more particularly, the invention relates to a system and method for communicating with a remote caller/client and then identifying the caller/client and the caller/client's location.

2. Description of Related Art

Many businesses provide products and services requiring that employees visit the recipients of the products and services. For instance, many health care providers send nurses to the homes of patients. Similarly, parcel delivery services deliver parcels directly to businesses and individuals. These businesses will frequently benefit from tracking when their employees arrive at and depart from particular locations.

U.S. Pat. No. 5,255,183 to Katz discloses a computer system for recording remotely, through a telephone network, the arrival and departure times of field based employees at various work sites. The system detects from a calling employee automatic number identification data (ANI) and further accepts personal identification codes from the caller. The ANI is used to identify the calling telephone.

Personal identification codes which are manually entered into a keypad can be entered by any individual. Accordingly, mere receipt of a manually entered personal identification code does not assure that the person entering the personal identification code is the person assigned to the personal identification code.

An ANI identifies the phone which made an incoming call. When the phone is a standard land line phone, the phone identity can be used to identify the address where the phone is located. However, if the phone used to make the incoming call is a cellular phone, the ANI alone cannot be used to determine the location of the phone.

A system and method for monitoring caller/clients is needed which can accurately identify the caller/client making the phone call and can identify the location of the phone call when the phone call is placed from a cellular phone.

SUMMARY OF THE INVENTION

A method for tracking a caller/client is disclosed. The method comprises the act of receiving a phone call from the caller/client. The method also comprises the act of receiving from the caller/client, a biometric identifier resulting from a unique physiological characteristic of the caller. The method further comprises the act of comparing the biometric identifier with a client database correlating clients with their physiological characteristics. The method also comprises the act of selecting which of the physiological characteristics in the client database corresponds to the caller/client identifier to identify the client.

A method for tracking clients is also disclosed. The method comprises the act of receiving a cellular phone call from a caller. The method also comprises the acts of identifying a caller/client geographic location of the phone call and comparing the caller/client geographic location with a database correlating addresses with geographic locations. The method further comprises the act of selecting from among the geographic locations included in the database the geographic location correlated with the caller/client geographic location to obtain an address.

A method for tracking a caller/client is disclosed. The method comprises the act of receiving a phone call from a caller/client. The method also comprises the acts of receiving a biometric identifier and a client identifier from the caller/client and identifying the origin of the phone call.

BRIEF DESCRIPTION OF THE DRAWINGS

FIGS. 7A–B illustrate a data structures for respectively Telco fixed and cellular databases.

FIG. 9 illustrates a report generated according an embodiment of the current invention.

DETAILED DESCRIPTION OF THE DRAWINGS

The invention relates to a system and method for tracking caller/clients as they visit the locations of various recipients. Caller/clients have access to telephones and identification devices which the caller/client can use to communicate with a remote computer. The computer uses information received during the communication to identify and authenticate the caller/client making the communication and the location of the caller/client.

Caller/clients can use the telephones and identification device to communicate identifiers which are unique to the client to the computer. The identifiers can result from some unique physiological characteristic of the client. For instance, the client can use a telephone to transmit a voice print. Similarly, the client can use an identification device to transmit a finger print or a retina print. The computer can use these identifiers to identify the client. Because each of these identifiers results from a physiological characteristic which is unique to the client, the system assures that the identified client is the client making the communication.

The system can include logic for identifying the address of a cellular phone at the time a phone call is placed. The logic does not require an automatic number identification (ANI). In fact, the ANI of a cellular phone may not provide any location information because the phone itself is mobile. Instead the logic uses information provided by the cellular carrier to identify the origin of the call with regard to the cell stations receiving the call. Accordingly, the client can be tracked when the client is using a cellular phone to communicate with the computer.

Figure 1:
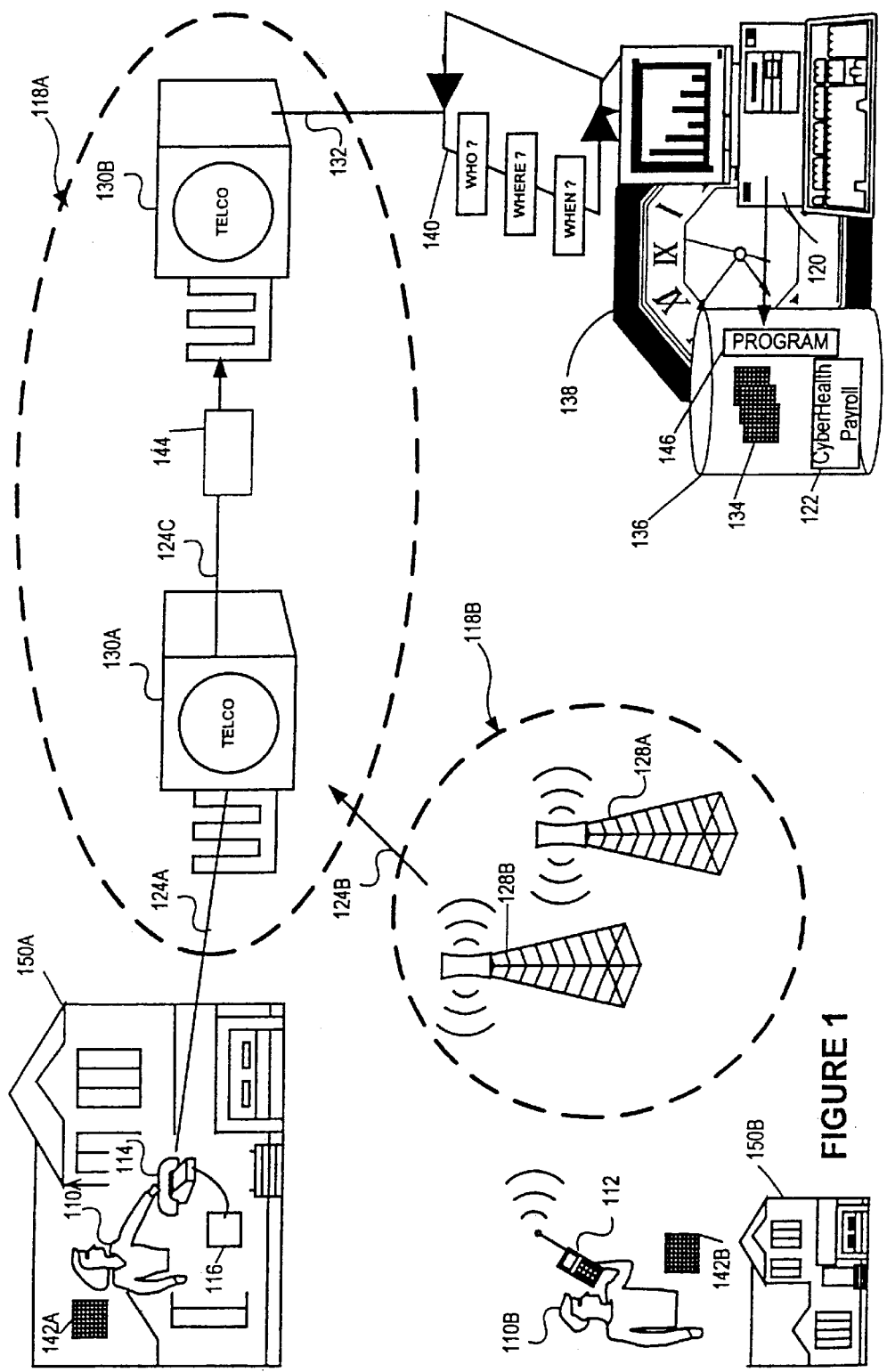
FIG. 1 shows an environment for practicing the current invention.

FIG. 1 illustrates a system for use of the present invention. The system includes a public switched telephone network (PSTN) for interfacing a computer 120 with cellular phone 112 and/or a standard plain old telephone service (POTS) phone 114. The PSTN includes wired segments 118A and wireless segments 118B. The wired segment includes central offices 130A–B connected over a digital backbone 124C such as the integrated services digital network (ISDN). Central office 130B is connected by modem link 132 to computer 120. Central office 130A is connected by analog subscriber line 124A to fixed phone 114 located at call site 150A. The wireless segment 118B includes a plurality of cells 128A–B each represented by a transceiver. Each of the cells is connected by a wired/wireless link 124B to central office 130A. Communications between cellular phone 112 at call site 150B and computer 120 are made across both wired and wireless segments of the PSTN. Either the fixed or cellular phone may provide an identification device. Biometric input device 116 is shown connected to fixed phone 114.

The computer 120 includes a timer 138 and a storage device 136. The storage device includes reports 122, databases 134, and program code 146 for implementing processes 140. The reports may include payroll reports. The databases may include employee biological parameters, geographic data, and payroll information.

The computer implements processes 140 for determining on the basis of information from a packet 144 received from the client: who called, when they called, where they called from, what they did when they were at the location, and how long they were at the location. Caller/clients 110A–B are shown with their respective unique biometric parameters 142A–B. Each of the clients has a unique biometric parameter. The biometric parameters may include for example, voice print, finger print, iris print, etc.

Biometric input device 116 allows a client to enter biometric parameters other than voice. For instance, the identification device can be used to electronically transmit information concerning the client's fingerprints and/or iris print. The identification devices can be included directly on the phones 112–114 or included in a base station included at the recipient's location. The identification device can also be carried by the clients 110A–B and include an interface which allows the identification device to communicate with the PSTN 118A or 118B.

In operation, the caller/clients 110A/B place a call upon arrival at the respective call sites 150A–B. The call site may be the home of a person who is ill or disabled and who is receiving a visit from a nurse. Alternately, the client 110A or 110B may be at the job site for a sales call, repair or for delivery of goods. Accordingly, the recipient can be an individual such as a patient, or a business such as a vendor. When the client arrives at the site they call a number corresponding to computer 120. The computer answers the call and receives the packets 144 (See FIGS. 4A–B) from the client.

The packets 144 contains information concerning the location of the clients 110A–B, the identity of the clients, whether the client 110A or 110B is arriving at or departing from the location and what tasks were performed during the time the client spent at the location. The system can be customized to provide additional information as desired by employers of the clients, or by the system administrators. The computer processes 140 combine the information in the packets with databases 134 to produce reports 122.

The reports 122 (See FIG. 9) may list the activity of the client by location, by recipient, by type of activity, and by duration of activity. In an embodiment of the invention the reports may be daily logs, which list the arrival and departure times of various clients 110A or 110B, of one or several different companies or divisions, at one more locations. Where a schedule database is provided, the reports may also list which of clients 110A–B were expected to but did not show up at, or spend the proper amount of time at a job site. Alternately, the reports may list the work site address, each employee's name, number, employment category, treatment type, etc. The reports 122 can be printed or transmitted to a remote location. The reports may include payroll reports. Alternately, the reports may be invoices to the recipient of the clients services. The reports 122 may be supplied to the client's employer so the employer can track the deliveries of the client 110 or the amount of time the client 110 spends with particular recipients. The employer can use the reports for payroll and/or for billing purposes. For instance, the recipient can be charged based on the amount of time the client spent with the recipient or based on the number of tasks the client performed while visiting the recipient.

Figure 2:
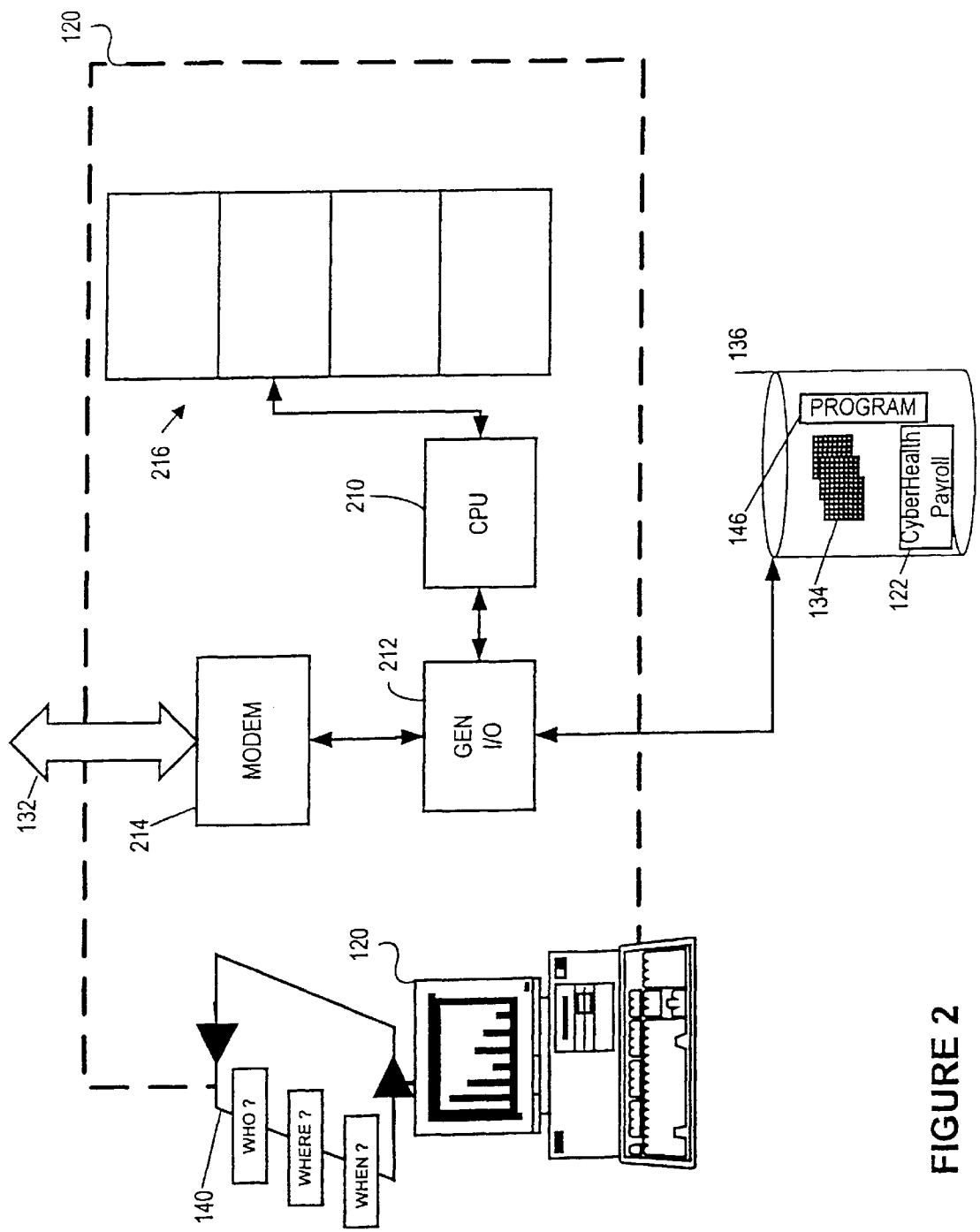
FIG. 2 is a block diagram of a computer configured to practice the current invention.

FIG. 2 shows details of computer 120. The computer includes a central processing unit (CPU) 210, general Input/Output (I/O) circuitry 212, a modem 214 and a volatile memory 216. The modem is coupled to the wired network 118A (See FIG. 1) over modem line 132. The modem communicates with the general I/O circuitry. The general I/O circuitry also communicates with the computer keyboard and with other standard computer peripherals. The general I/O circuitry also communicates with storage device 136. The CPU is coupled both to the general I/O circuitry, as well as to the volatile memory 216. The volatile memory is utilized during execution of the program code 146. The program consists of computer instructions for implementing the computer processes shown in the following FIGS. 11A–C. The program code 146 also includes instructions for communicating with standard, off the shelf application programs available from various vendors, for example, application programs which control the telephone I/O circuitry 212 and data base handling software programs.

Suitable modem 214 hardware includes, but is not limited to, one or more DIALOGIC 4XX, or 2XX multi-line voice communication system boards and DIALOGIC's MF daughterboard and DIALOGIC's DTI 124. These boards are designed to operate with an IBM compatible line of personal computers, or similar computer systems, and are available from the Dialogic Corporation of Parsippany, N.J. The DIALOGIC 4XX and 2XX multi-line voice communication system boards relieve a system designer from the tasks of having to freshly design various software and hardware for communicating over telephone lines. These boards are capable of handling multiple tasks simultaneously, i.e., simultaneously receiving and processing information from a number of telephones. A description of the DIALOGIC telephone and voice communication hardware and software including its Voice Communications System, Multi-Line, Digital Telephoning Interface, and MF Interface boards is contained in DIALOGIC data sheets which can be obtained by dialing 201-334-8450 or writing to Dialogic Corporation, 300 Littletown Road, Parsippany, N.J. 07054. These data sheets are incorporated by reference as if fully set forth herein. Suitable software for use with the invention includes, but is not limited to Vbase/40, which is also available from the Dialogic Corporation and has been used in conjunction with the aforementioned DIALOGIC/40 hardware.

Figure 3:
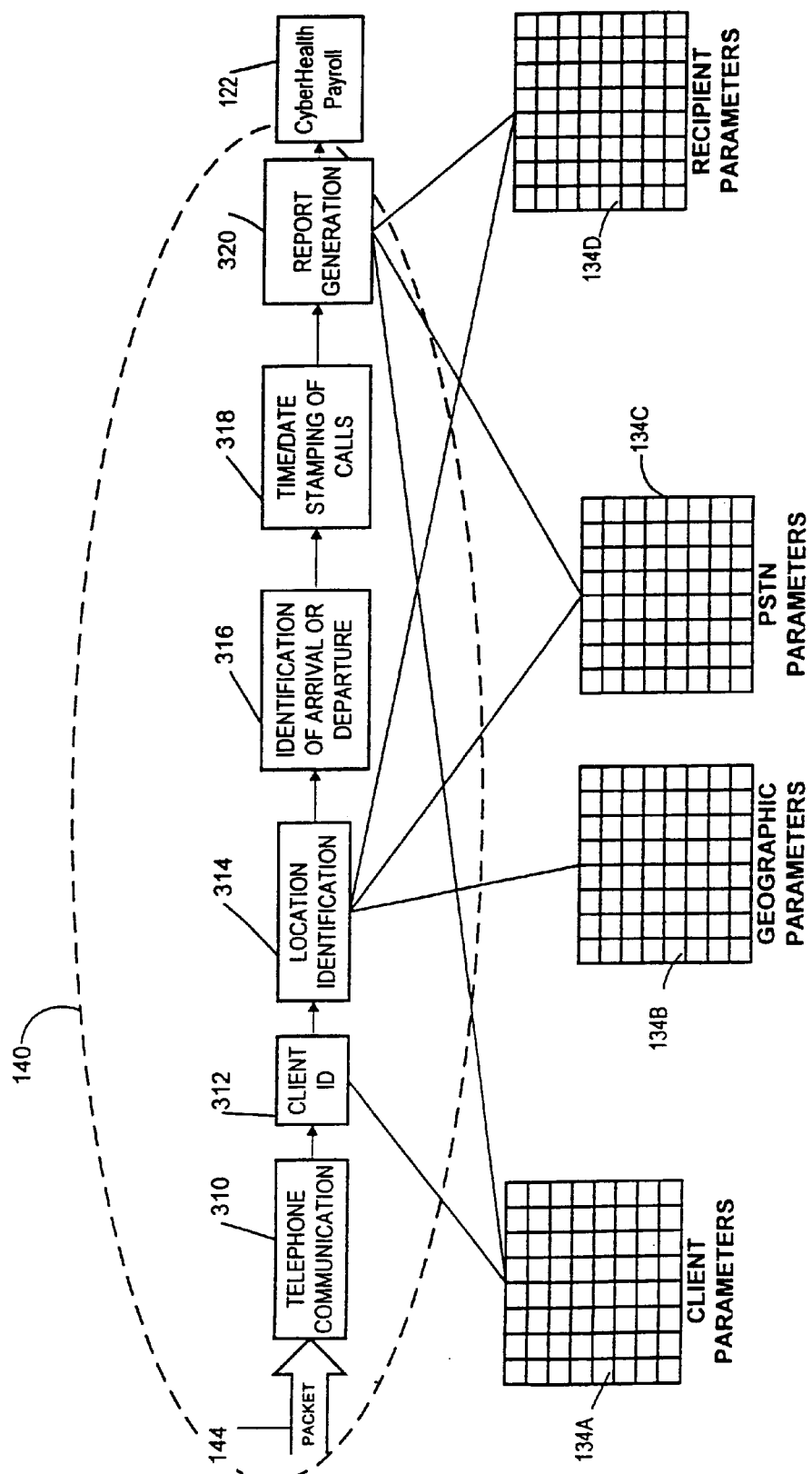
FIG. 3 illustrates software modules associated with an embodiment of the current invention.

FIG. 3 shows an embodiment of the software modules associated with processes 140 (See FIG. 1). Telephone communication module 310, client identification module 312, location identification module 314, arrival and departure identification module 316, time and date stamping module 318, and report generation module 320 are shown. The modules are shown coupled in serial order. As will be obvious to those skilled in the art, the modules may be executed serially in several arrangements or in parallel.

The telecommunication module 310 is coupled to the PSTN to receive packets 144 in the incoming phone call from either of clients 110A–B (See FIG. 1). The telephone communication module 310 initializes the modem 214 to enable telephone communications. Incoming packets 144 are presented by the telecommunication module to the client identification module 312. The client identification module 312 identifies the client 110A/B which is calling. The client identification module interfaces with a client database 134A (See FIG. 1) to match a client biometric parameter, e.g. voice (see FIG. 5, Ref. 142 A/B) with a corresponding biometric parameter, e.g. a voice print, in the client parameter database. Associated with each voice print is a corresponding client identifier, and other relevant client information (See FIG. 5).

The location module may interface with the geographic database 134B (See FIG. 6), the PSTN database 134C (See FIGS. 7A–B), and the recipient database 134D (See FIG. 8) to obtain the location of the client. The location of the client may be in the form of a recipients address, a street address, a longitude and latitude, etc. The arrival and departure module 316 determines whether the clients 110A/B are arriving at or departing from the recipient's address. The time and date stamping module 318 determines the time of the phone call and correlates that with the client identity and location.

The report generation module 320 creates the reports 122 which may include for example: payroll reports, time and attendance reports, invoices and exception reports. Exception reports include for example, reports as to those calls not authenticated, or calls without a complementary arrival or departure entry. Exception reports can also include reports which list those records for which the task codes entered seem inappropriate and possibly fradulent. For example computer 120 has access to a database 134 which lists for each task code an estimated time to perform then the estimated time to perform can be compared to the duration of the visit at the call site. If the time at the call site is much less than the estimated time to perform then the record can be placed in the exception report for further investigation. Thus an exception report can be used to control cost overruns. The report generation module interfaces with the client, PSTN and recipient databases. It may also interface with additional databases containing for example client wage rates and federal state and local tax information.

FIGS. 4–8 illustrate the data structures for a plurality of databases stored in the volatile memory 216. These databases can be modified by the computer 120, or can be administratively modified through use of a keyboard.

Figure 4A:
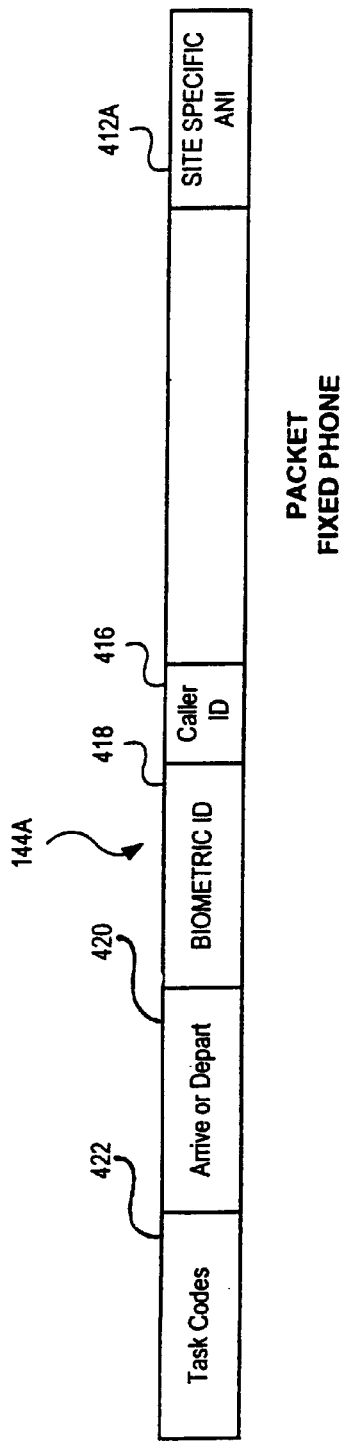
FIGS. 4A–B illustrate a data structure for incoming packets from respectively a fixed and a cellular phone.
Figure 4B:
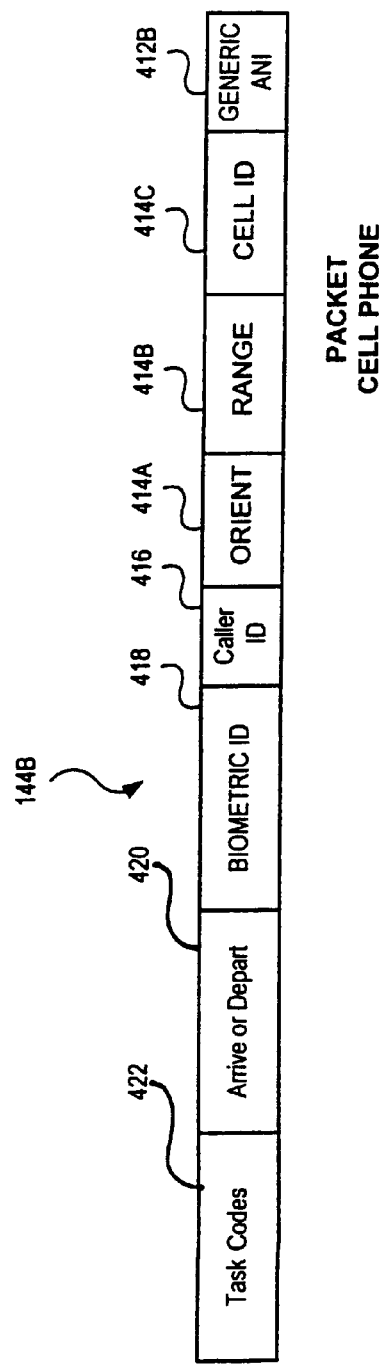

FIGS. 4A–B illustrates an embodiment of the contents of respectively a fixed/standard phone packet and a mobile/cellular phone packet. The information received need not adhere to a rigid structure, nor include each and every field to be discussed. The information shown in FIGS. 4A–B is received by the computer 120 when answering an incoming phone call. The received information data structure of packet 144A for a fixed phone 114 (See FIG. 1) includes a site specific ANI field 412A, a client identifier field 416, a biometric identifier 418, an arrival or departure indicator field 420 and a task code field 422. The site specific ANI field 412A may contain the phone number of the caller. In the case of a fixed phone this will correlate with the recipient's address, and is therefore site specific. The identifier field 416 may include information in the form of a numeric sequence entered by touch tone to identify the caller. The numeric sequence need not be entered by touch tone only. Instead the user can be prompted by processes 140 (See FIG. 1) to vocalize the numeric sequence which will be processed and converted to numbers by voice recognition processes. Alternately, the first client identifier may be a numeric sequence corresponding to the clients employer. In another embodiment, the first client identifier may be a unique tone generated audibly by a "whistle" possessed by the client and placed up to the microphone of the phone. This whistle could include pitch, tone, and sequence to uniquely, audibly identify the client. Of course the problem with the first client identifier, is that it does not authenticate the clients identity. Anyone in possession of the whistle or the employer's name/code or the employee's name or code can input the code by touch tone pad or audibly and thus generate a false attendance record in the computer. In another embodiment the first client identifier is not required at all. Instead the biometric identifier is used to identify the caller/client.

To authenticate a client's identity the biometric identifier 418 is provided. This field contains information unique to the client such as voice print, thumb print and iris print. In the case of a voice print, no separate field per se is present in the incoming packet 144A. Instead, a sample of the client's speech is obtained during the call session and turned into a voice print for comparison with the voice prints in the client database to find a match. (See FIG. 5). Voice prints may be obtained by well known techniques such as spectral analysis in which the sample is subject to Fourier transformation in which the main spectral components and amplitude of the clients speech are sampled. Thumb prints and iris prints may be obtained by external devices such as biometric input device 116 (See FIG. 1) which converts visual data on the thumb or eye to electronic information and transmits that information over the phone line.

The arrival and/departure field is an optional field which if provided will speed up the determination of the sequencing of the call. The client may for example indicate when the call corresponds to arrival at a site by pressing the "#1" key sequence and when the call corresponds to departure by the "#2" key sequence. The task code field is also optional and may indicate the category of work performed at the site. This information also may be entered in the form of "#_" key sequences, and is useful in computing charges for work/services/products delivered/purchased at the call sites 150A/B (See FIG. 1) by the recipients.

FIG. 4B shown the information that may be retrieved in an embodiment of the invention when the incoming call is placed from a mobile/cellular phone 112, or pager with limited call back capability. The information is identical to that described above in connection FIG. 4A, except for fields 412B and 414AC. A mobile call, like a fixed phone call, is preceded with an ANI identifying the calling number. In the case of a cellular call, the number does NOT provide information as to location, and thus may be useless to process. Of course if the cellular phone is assumed to be solely in the client's possession then the generic ANI in field 412B may serve as and be substituted for the client identifier 416. Because the ANI may not be used to indicate location other information must be provided. That information is provided by complying cellular carriers and included in the packet 144B at the start of a call originating from a cellular/mobile phone. In an embodiment of the invention, the information comprises a received cell identifier field 414C, a range field 414B and a call site orientation field 414A. The cell identifier field 414C lists an identifier for the transceiver picking up the call. The range field 414B gives the distance from the cell to the call site 150B, and the call site orientation field gives the orientation from the cell to the origin of the call site 150B in degrees, 0–360. This information is used to define the coordinates of call site 150B (See FIGS. 1, 10B). In another embodiment of the invention, the information provided in field(s) 414 could include multiple cell IDs and either range or orientation information from each to the call origin (See FIG. 10A). This also would allow a call origin to be determined by triangulation. In still another embodiment of the invention, the phone company could directly provide the coordinates of a call origin.

In operation, the computer 120 answers an incoming phone call from a client 110. The computer 120 receives an ANI before the phone call is answered and then stores the ANI in the ANI field 412. An ANI is a telephone related system and protocol by which the telephone number of the calling party is supplied to the called party before the called party answers the telephone call. Accordingly, the computer 120 can use the ANI to determine the phone number of the phone used to make the incoming phone call.

When the call originates from a cellular phone 112, the computer 120 receives the cell locator and stores it in the cell locator fields 414A–C. The cell locator is used to determine the geographic location of the cellular phone 112 used to make the phone call. A signal providing the cell locator information can be provided at each cell 128 monitoring the phone call. The signal follows the ANI and can be delivered to the computer 120 before the computer 120 responds to the phone call.

In operation, the computer 120 can optionally receive a first identifier and store it in the received client identifier field 416. The received first identifier can be a code entered into the phone keypad. The code can be unique to a particular client 110 or to a group of clients. The first identifier can be used to define a client database subset limited to client database rows which including the received first identifier.

In operation, the computer 120 receives a biometric identifier and stores it in the received biometric identifier field 418. The biometric identifier results from some physiological characteristic which is unique to the client 110. Suitable second identifiers result from the client's voice, fingerprints and retina.

The computer 120 can also receive an arrival or departure indicator and store it in the arrival or departure indicator field 422. The arrival or departure indicator indicates whether the client 110 is arriving at the location or is departing from the location. Suitable arrival or departure indicators include, but are not limited to, specific codes entered into the pad of the phone. For instance, a numeral 1 can indicate arrival while a numeral 2 can indicate departure. The entry of the arrival or departure indicator can be prompted by the computer 120 as described above.

The computer can also receive task performed codes and store them in a task code field 422. The task performed code can be as simple as a code which is specific to each task the client performs while with the recipient. For instance, the client can use the phone keypad to enter the numeral 1 when the recipient was given medication and the numeral 2 when the recipient's bedding was changed.

Figure 5:
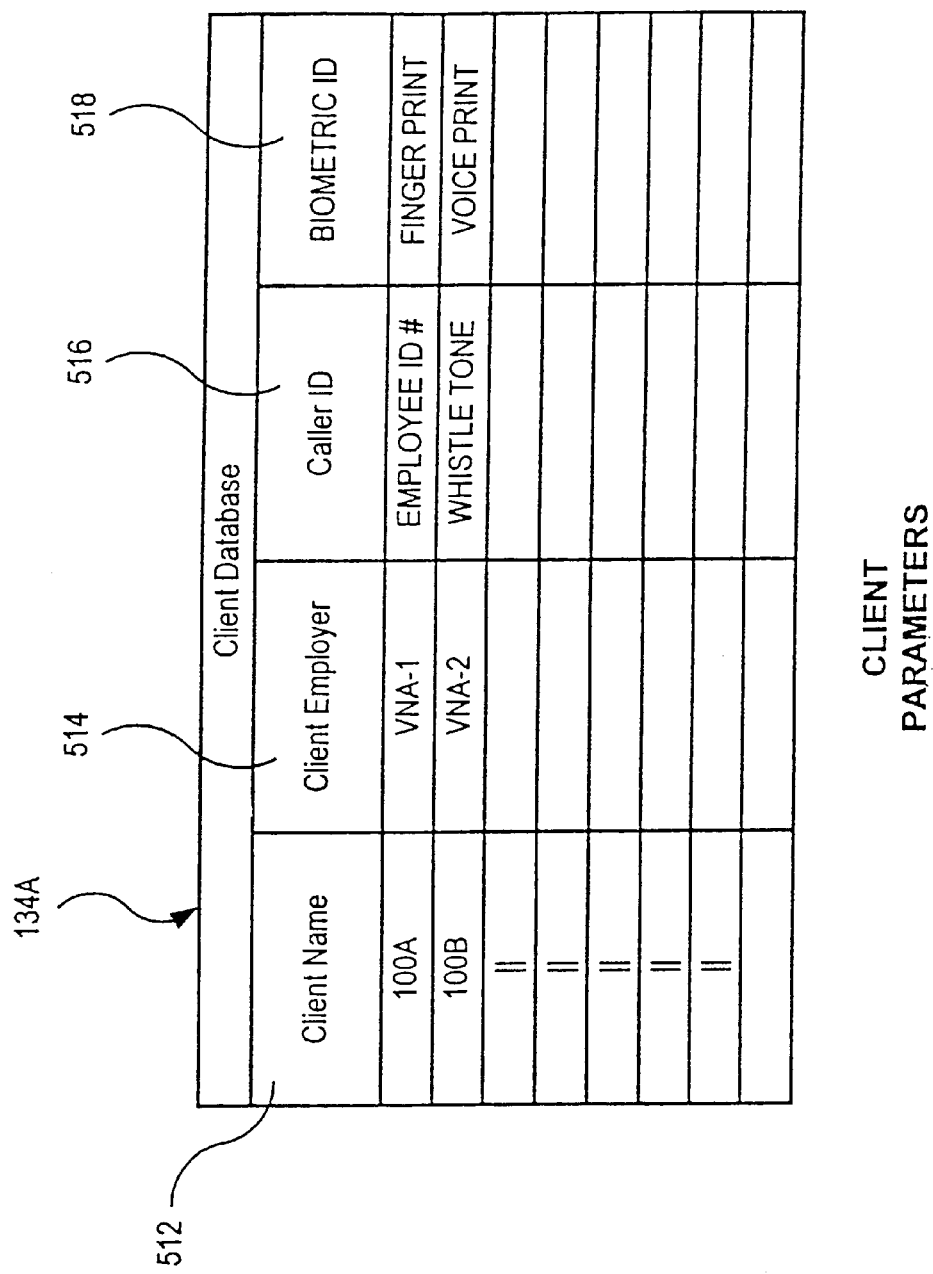
FIG. 5 illustrates a data structure for a client database.

FIG. 5 illustrates a data structure for a client database 134A included in the storage device 136. The client database contains records that allow callers to be identified. Each record of the client database includes a client name field 512, an employer field 514, a caller ID field 516 and a biometric identifier field 518. The client name field lists the name of the client 110A–B. The employer field 514 lists the name of the client's employer. The first identifier field 516 lists a first identifier. The caller ID can be a code which is unique to a particular client 110A–B or to a particular group of clients. The caller ID can be unique to a particular employer and can be used by all that employer's clients. The use of a first identifier is optional, accordingly, the first identifier column may be left blank. The biometric identifier field 518 lists addresses where biometric samples for each client 110 can be found. The samples can include addresses for files containing voice print samples/patterns, fingerprint samples/patterns, and iris samples/patterns, retina print samples/patterns, and ear print pattern/samples. These may be stored electronically, optically etc. The caller/client ID identifier field can be used to reduce the number of fields which must be searched to find a match between a biometric identifier received by the computer from an incoming packet 144 and a second biometric identifier listed in the client database 134A.

Figure 6:
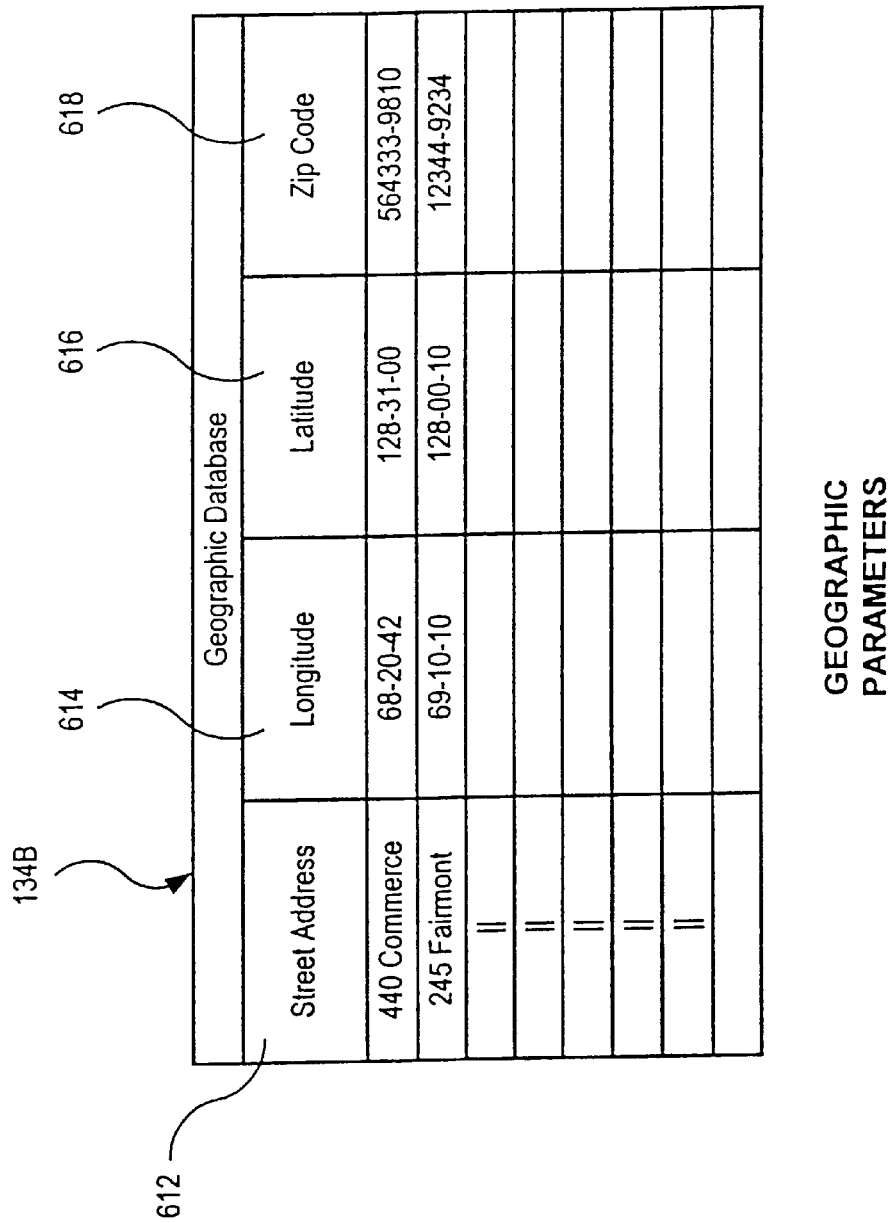
FIG. 6 illustrates a data structure for a geometric parameter database.

FIG. 6 shows several records in the geographic database 134B which is used for determining call origin coordinates/location for cellular phone calls. Each record of the geographic database includes a street address 612, and a corresponding longitude 614, latitude 616 and zip code 618. The records in the geographic may be regional, national or international in scope. Once the coordinates of a cellular call origin are determined this database allows the coordinates to be translated into a corresponding street address (See FIG. 11B).

FIGS. 7A–B illustrate the PSTN database data structures for respectively the phone # and PSTN address database 134C1 and for the cell # and PSTN location database 134C2. Both of these databases may be included in the storage device 136.

Each record of the phone # and PSTN address database 134C1 includes a phone number field 712, a subscriber name 714, a subscriber address 716, and a cellular/fixed indicator 718. Given a site specific ANI (See FIG. 4A) from a fixed/standard phone call, this database can be used to determine the address of the call origin. The entries in the database may be limited to eligible phone numbers corresponding to known clients and recipients, or may include all numbers in the PSTN service area. Field 718 indicates whether the phone number corresponds to a cellular phone 112 or a fixed phone 114. In the former case, the subscriber address field 716 may not indicate call location since the phone is mobile, while in the latter case it does. Some recipients will not have a phone but will be serviced by a client 110A/B with a cellular phone 112.

FIG. 7B illustrates a data structure for a record in the cell number and PSTN location database 134C2, which may also be stored in storage device 136 (See FIG. 1). Each record may include a cell identifier 730 and the geographic location 732, e.g. address or longitude and latitude, of the transceiver servicing the cell. The cell identifier is a code which is unique to a particular cell 128A/B (See FIG. 1).

Figure 8:
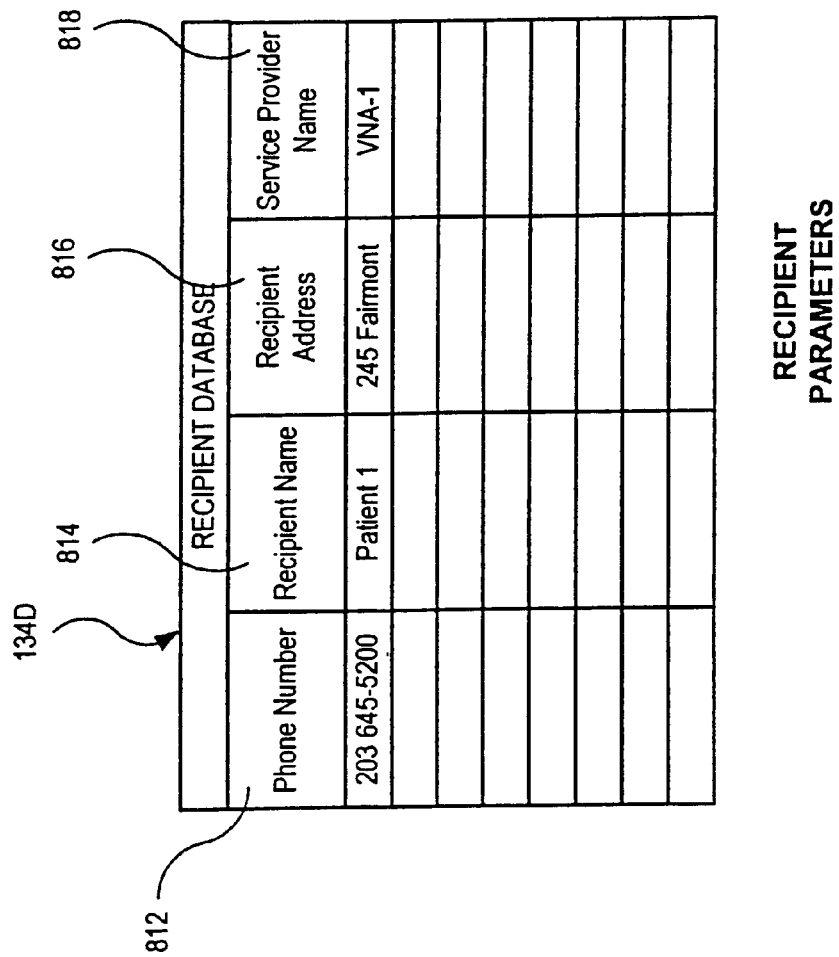
FIG. 8 illustrates a data structure for a recipient database.

FIG. 8 shows an embodiment of the recipient database 134D (See FIG. 1). This database is utilized by the location identification module 314 and report generation module 320 (See FIG. 3). Each record of the database includes a phone number 812, a recipient name 814, address 816, and the name of the service provider 818 for the recipient. The service provider field is optional. In the example shown, the recipient is a patient, e.g. Patient 1, receiving home health care from a visiting nurse association (VNA), e.g. VNA 1.

FIG. 9 illustrates the data structure of the records in an embodiment of the report 122 generated in accordance with the current invention. Each record includes: a client name fields 912, an employer field 914, a recipient address field 916, a recipient name field 918, an arrival time field 920, a departure time field 922, a time spent with recipient field 924 and a tasks performed field 926. The arrival time field lists the time the client 110A/B arrived at the recipient's address. The departure time field lists the time the client 110A/B departed the recipient's address. The total time spent with client is computed by differencing the departure and arrival time, and is recorded in field 924. This field can be used to generate payroll, if combined with corresponding wage and tax information. The tasks performed field describes the tasks which the client performed while the client was with the recipient. In the case of a VNA different tasks may be reimbursed at different rates. The tasks also indicate method/manner of treatment which itself may be used to generate other reports.

Figure 10A:
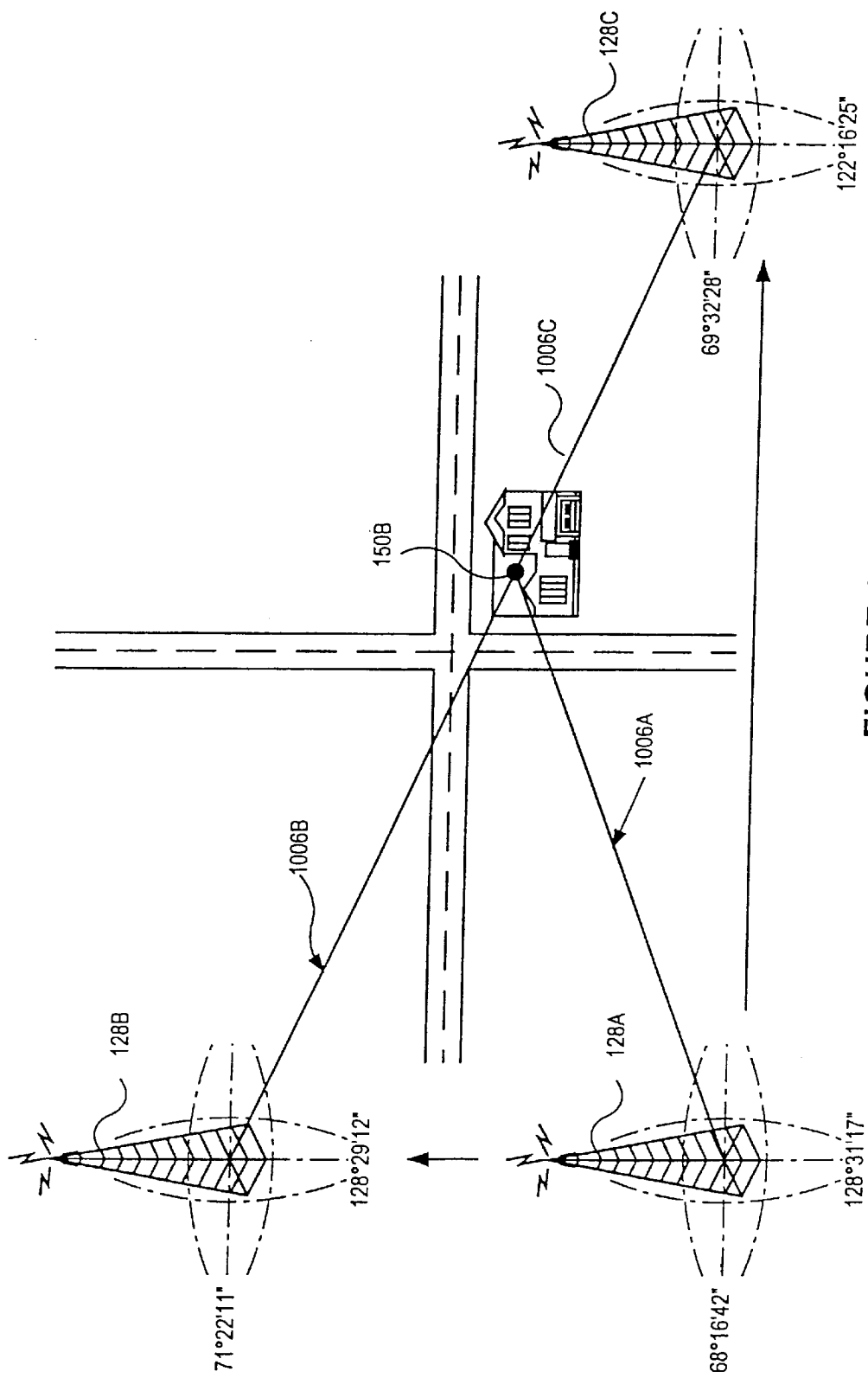
FIGS. 10A–B illustrate alternate embodiments for locating the origin of a cellular call.
Figure 10B:
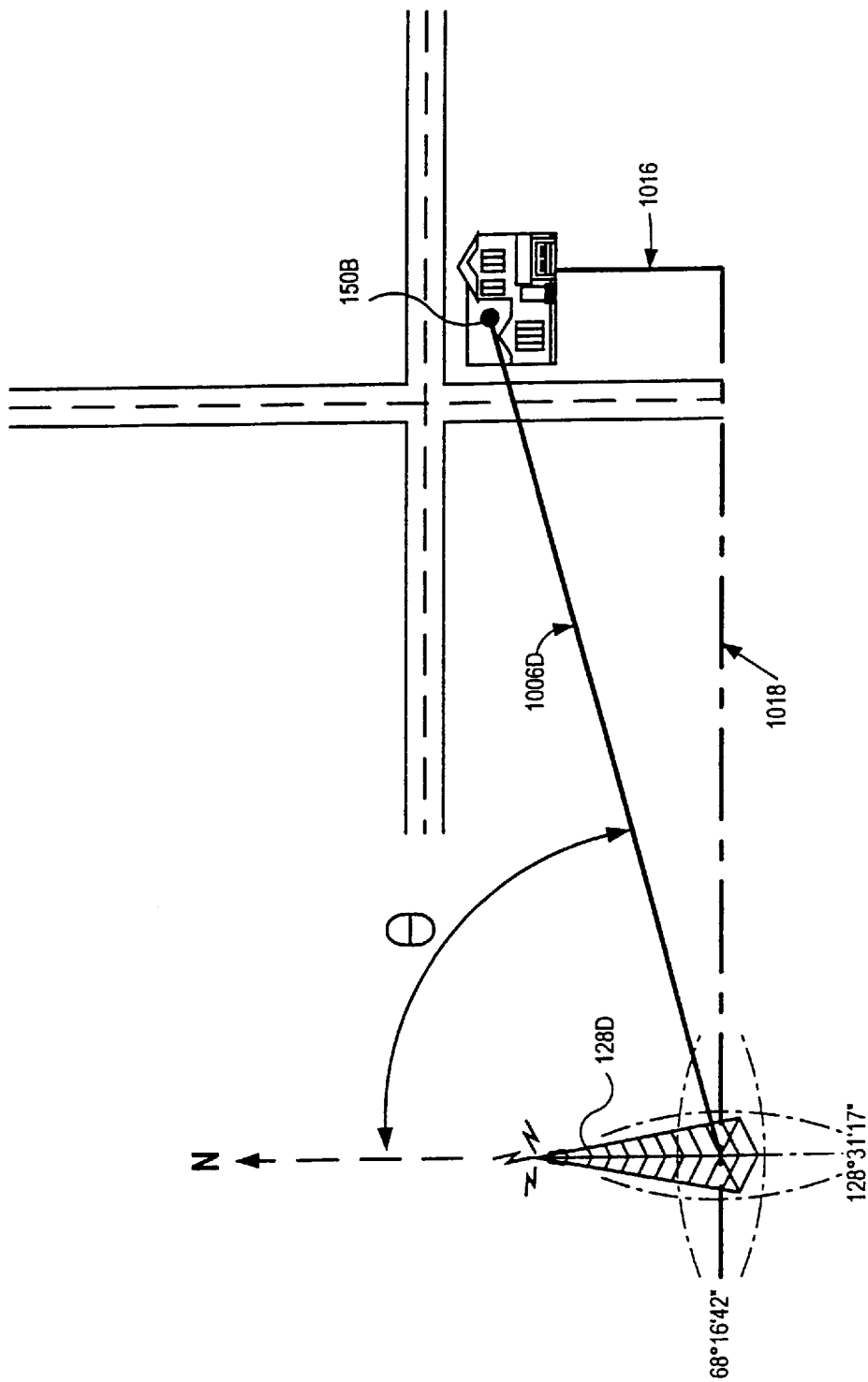

FIGS. 10A–B show alternate methods for deriving call origin information from a cellular call based on information provided by the PSTN about transceiver location, call range, and/or call origin.

A cellular phone call made from a recipient's home 150B is illustrated in FIG. 10A. The signal strength is monitored at the cells 128A–C and specifically the transceivers servicing the cells. The signal strength at each cell is monitored and the cell receiving the strongest signal services the call. When the caller is moving relative to the cells, the cell servicing the call can be changed so the call is always served by the cell receiving the strongest signal. The cell can include logic for translating the signal strength into an approximate range 1006A–C of the client 110B from the cell. When only range information is provided, a circle is computationally projected around each cell. Each circle has a radius corresponding to the range from the receiving cell. The point of intersection of the circles is the call origin. Using techniques well known to the prior art the coordinates of each cell, which are contained in the PSTN cellular database 134C2 (See FIG. 7B) can be translated into call origin coordinates. These calculations to establish call origin can be performed solely on either the PSTN or by the PSTN in combination with processes 140 (See FIG. 1). The location information is passed by the PSTN in packet 144 to the computer 120. Alternately, where each cell includes 3 antennas spaces 120 degrees apart only two cells are required to define a location in terms of longitude and latitude.

An alternate embodiment of cellular call origin location is illustrated in FIG. 10B. When a cell is configured to monitor range and orientation of call origin, the information provided by a single cell may be sufficient to locate the origin of a call. The orientation of the caller can be expressed as an angle, $\theta$, relative to some direction such as North. The cell 128D can include logic for translating the signal strength into an approximate range of the client 110B from the cell 128D. The range 1006D and client orientation can be used as polar coordinates to calculate a latitude displacement 1016 and a longitudinal displacement 1018 of the origin of the call site 150B for the client 110B from the cell 128D.

Figure 11A:
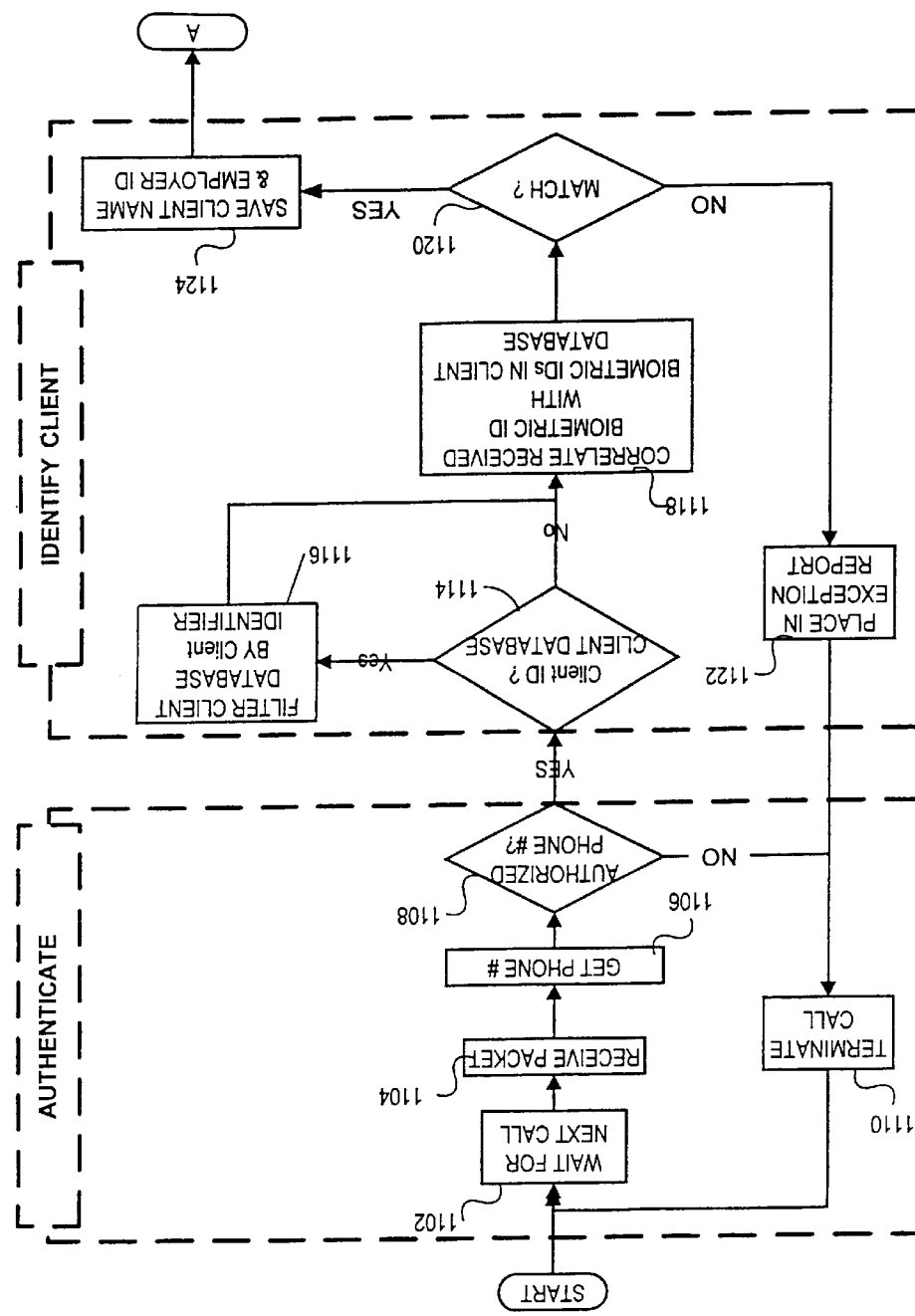
FIGS. 11A–C show the process flow associated with identifying a caller, a location of the call, and the duration of the stay of the caller at the location according to an embodiment of the current invention.
Figure 11B:
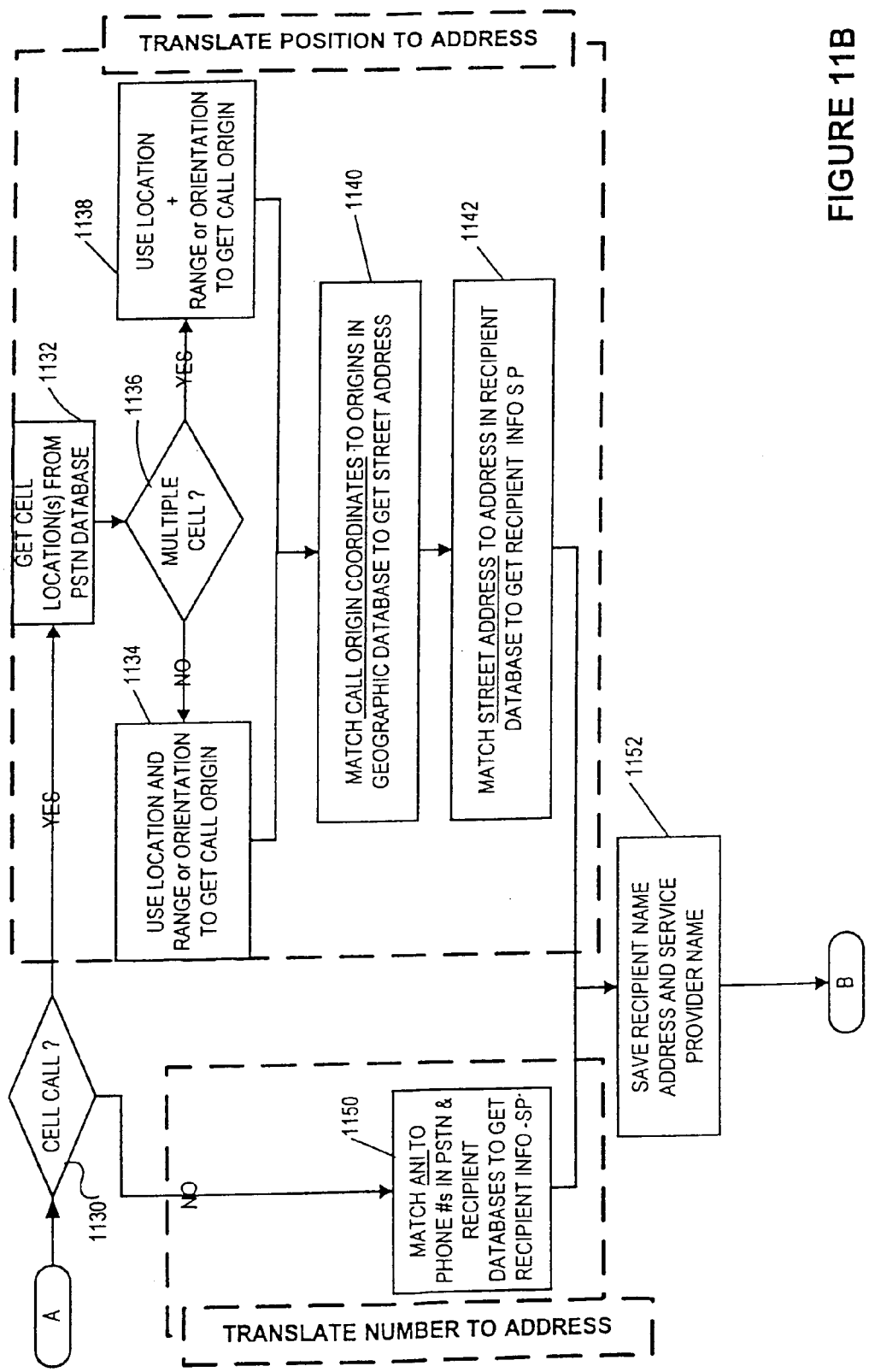
Figure 11C:
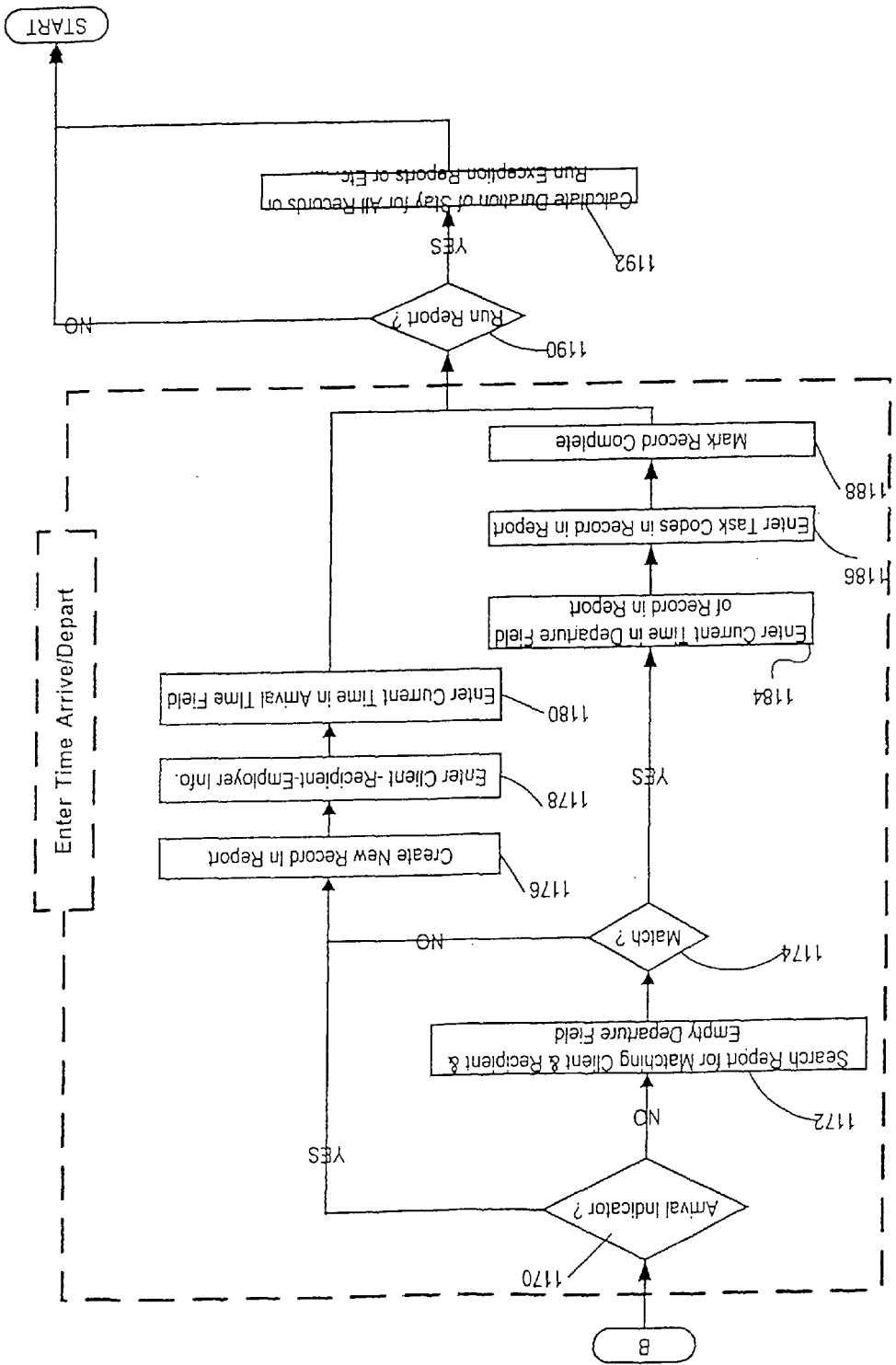

FIGS. 11A–C show processes associated with implementing client identification, location identification and duration of stay calculations associated with an embodiment of the current invention. From a start block, control is passed through an authentication routine comprising processes 1102–1110. Commencing with process 1102 a determination is made that the next call has been received. Control is then passed to process 1104. In process 1104 the packet 144 from either a fixed or a cellular phone (see FIGS. 4A–B) is retrieved. Control is then passed to process 1106. In process 1106 the phone number of the fixed or cellular phone from which the call is placed is retrieved. Control is then passed to decision process 1108. In decision process 1108 a determination is made as to whether the received phone number is eligible for further processing, e.g. is contained in PSTN database 134C1 (See FIG. 7A). In the event this determination is in the negative, control is passed to process 1110. In process 1110 the call is terminated. Subsequently control returns to process 1102 for the processing of the next call. Alternately if in decision process 1108 an affirmative decision is reached, i.e. that the phone call is authorized then control is passed to the next subroutine. In an embodiment of the invention, call authentication involves checking the phone number of the incoming call against a list of approved phone numbers. In certain areas of the country, ANI is not available for incoming calls and in this event the processes associated with authentication may be performed later on in the processing after, for example, identifying the client.

Control is then passed to the next subroutine and associated processes 1114–1124 for identifying the client making the call. In the client identification processes 1114–1124 processing begins at decision process 1114. In decision process 1114 a determination is made as to whether the incoming data packets contain a first client identifier (see FIGS. 4A–B, field 416). The first client identifier may for example be a touch tone sequence entered by a caller which corresponds to a client ID. Alternately, this sequence may be entered by the caller without using the touch tone pad if at the recipient site there is an audible numeric recognition system. The first client identifier may also be a unique whistle or tone pattern generated by a device in the possession of the client and broadcast over the phone line. The client identifier may also be a numeric sequence corresponding to the client's employer or service provider. If there is a first client identifier then control is passed to process 1116. In process 1116 the client database shown in FIG. 5 is filtered so that only those entries having a first identifier matching the first identifier retrieved in process 1104 remain. Control is then passed to process 1118. Control is also passed to process 1118 if a negative determination is reached in decision process 1114, i.e. that no first identifier is present in the incoming packet. In process 1118 using either the whole or the filtered database the biometric data received in the incoming packets in process 1104 is utilized to determine the identity of the client making the call. As discussed above, the use of biometric data overcomes the security problem associated with merely relying on a fixed number sequence to identify a client. A fixed number sequence is subject to theft and duplication whereas biometric data suffers none of the above shortcomings and is unique to the individual making the call. If the person making the call is using an auxiliary device, e.g. device 116 for entering biometric data such as fingerprint or iris print then that information is correlated with biometric information in the client database (see FIG. 5) to find a corresponding entry. If a stand-alone biometric entry device, e.g. device 116, is not being used then biometric data is obtained by taking the user's voice print from the incoming packets retrieved in process 1104. That print is processed according to any one of a number of well-known prior art processes such as spectral or phase or phoneme matching to find a corresponding entry in the client database. Control is then passed to decision process 1120. In decision process 1120 determination is made as to whether a match between the biometric data and the incoming packet and the biometric data in the client database has been made. A match is a binary yes/no conclusion reached on the basis of a acceptable degree of confidence that the stored biometric data matches the biometric data in the incoming packet 144. In the event a negative determination is reached, control is passed to process 1122. In process 1122 an exception report is generated which shows those authorized entries in which client identification was not possible. Control returns from process 1122 to process 1110 in which the call is terminated. If alternatively the biometric data in the incoming call matches the biometric data of a client in the client database then control is passed to process 1124. In process 1124 the client name and employer ID and other information associated with the matching entry in the client database (see FIG. 5) is retrieved for use in subsequent processes shown in FIGS. 11B–C. Control is then passed to splice block A.

Processing in FIG. 11B begins at splice block A from which control is passed to decision process 1130. In decision process 1130 a determination is made as to whether a cellular or fixed call is being received. This determination may be made on the basis of information received in the incoming packets. The information may, as shown in FIG. 7A, be based on the fact that the ANI in the incoming packet 144 corresponds to a record in the PSTN database 134C1 which lists the number as cellular, e.g. field 718. Alternatively, the decision may be made on the basis of cell ID, range and orientation information in the incoming packet 144 which indicates the cellular origin of the call. In an embodiment of the invention shown in FIGS. 4A–B, cellular phone companies will provide additional information with the incoming call packets such as shown in FIG. 4B. Alternatively, as will be obvious to those skilled in the art, the cellular service providers may provide call origin location directly either in the form of longitude and latitude coordinates or street address. Alternately, the cellular phone providers may have a unique identifier in the generic ANI field 412B (See FIG. 4B) which identifies the origin of the call as cellular. If a determination in the affirmative is reached, that the call is cellular, then control is passed to a subroutine for translating position to address of call origin. The processes 1132–1142 are associated with this subroutine. Alternately, if the call is not cellular in origin control is passed to processes for translating an ANI directly to an address associated with the origin of the call.

If the call is cellular then translation of position to address begins at process 1132. In process 1132 the location information provided by the cellular carrier in the incoming packet 144B and shown in fields 414A–C (See FIG. 4B) is retrieved from the incoming packet. Control is then passed to decision process 1136. In decision process 1136 a determination is made as to whether the location information provided by the cell company is in the form of a multi-cell or single cell identification sequence. If a multi-cell identification sequence is provided then control is passed to process 1138. If a single cell sequence is indicated then control is passed to process 1134. Information corresponding to a single cell sequence could for example include cell ID, range from the cell and orientation from the cell as shown in fields 414A–C in FIG. 4B. Alternately in a multi-cell sequence a plurality of cell IDs would be accompanied by corresponding range or orientation information.

In process 1138 the calculation of a call origin using a plurality of cell sites is accomplished. If each cell site is identified by longitude and latitude and range information to the point of origin then processing proceeds as follows. Computationally from each cell site a circle having a radius corresponding to the indicated range is projected around each of the cells identified in the incoming packet. An intersection is calculated and the longitude and latitude for that intersection is determined. Control is then passed to process 1140. Alternately if orientation information, rather than range, is provided in the incoming packet 144 for a plurality of corresponding cells, then processing proceeds as follows. For each cell a vector corresponding to the orientation information provided in the incoming packets is computationally projected. Then the intersection of the plurality of vectors from each corresponding cell is determined and a longitude and latitude for that point of intersection is calculated. Control then also passes to process 1140.

If alternately in decision process 1136 a determination is made that an incoming packet contains single cell information than control is passed to process 1134. Single cell information may for example consist of longitude and latitude information for a single cell site and range and orientation information for the call origin with respect to the cell. Using this information a longitude and latitude is derived for a call origin. Control is then passed to process 1140. In process 1140 the geographic database shown in FIG. 6 is analyzed to find a street address with longitude and latitude coordinates matching those calculated in either of processes 1134, 1138. Control is then passed to process 1142. In process 1142 the street address obtained in process 1140 is utilized to find a record having a matching street address in the recipient database shown in FIG. 8. Control is then passed to process 1152.

If in decision process 1130 a negative determination is reached, i.e. that a fixed phone call is being processed rather than a cellular call, then control is passed to the subroutine for translating phone number directly into address. Processing is conducted in process 1150. In process 1150 the ANI from the incoming packet is matched against phone numbers in the PSTN database 134C1 shown in FIG. 7A. Alternately the ANI may be compared directly with phone numbers in the recipient data base shown in FIG. 8. When a matching record is found in the recipient database control is passed to process 1152. In process 1152 the recipient name and address and the associated service provider name from the recipient database shown in FIG. 8 is saved. Control is then passed to splice block B.

Determination of arrival and departure times and duration of stay are shown in FIG. 11C. From splice block B control is passed to a subroutine including processes 1170–1188 for determining arrival and departure times of a client at a specific site. From splice block B control is passed directly to decision process 1170. In decision process 1170 a determination is made as to whether an arrival indicator is present in the incoming data packet. As discussed above, this may be a unique DTMF sequence in incoming call packet such as referred to in FIG. 4A, and specifically field departure indicator field 422 thereof. If a determination is reached that there is an arrival indicator then control is passed to process 1176. In process 1176 a new record is created in the report shown in FIG. 9. Control is then passed to process 1178. In process 1178 client recipient and employer information obtained in processes 1118 and 1152 (see FIGS. 11A–B) is entered into the record in the report. Control is then passed to process 1180. In process 1180 the current system time is entered into a corresponding arrival time field 920 (see FIG. 9) of the new record. Control is then passed to decision process 1190.

If alternately in decision process 1170 an arrival indicator is deemed not to be present in the incoming packet then control is passed to process 1172. In process 1172 determination is made by searching the report as to whether a record having a matching client and recipient and an empty departure time field is present in the report. Control is then passed to decision process 1174. In decision process 1174 a determination is made as to whether there is any matching entry in the database. In the event this determination is in the negative control is passed to processes 1176–1180 for the creation of a new record in the report. If alternately a determination is made in decision process 1174 that a matching entry is present in the report then control is passed to process 1184. In process 1184 a current system time is entered into the corresponding departure time field 922 (See FIG. 9) of the report. Control is then passed to process 1186. In process 1186 the task codes obtained from the received packet in process 1104 (See FIG. 11A) are appended to the corresponding fields 926 (See FIG. 9) of the record in the report. Control is then passed to process 1188. In process 1188 the record is marked as complete in the report. Control is then passed to decision process 1190.

In decision process 1190 determination is made as to whether a user has prompted for the generation of a report. If that decision is in the negative then control returns to the start block (see FIG. 11A). Alternately if in decision process 1190 a determination is made that a report needs to be run, then control is passed to process 1192. In process 1192 all complete records are processed and the interval between the arrival and departure time of each record is calculated. When the time at site information thus calculated is combined with wage and tax information the report generated may become a payroll report. Alternately, report generation processes can include the generation of exception reports to indicate possibly fraudulent task code entrys, or to indicate unauthenticated records, or incomplete records. Subsequent to the production of a report control returns to the start block (See FIG. 11A).

While the present invention is disclosed by reference to the preferred embodiments and examples detailed above, it is to be understood that these examples are intended in an illustrative rather than limiting sense, as it is contemplated that modifications will readily occur to those skilled in the art, which modifications will be within the spirit of the invention and the scope of the appended claims.

What is claimed is:

1. A method tracking clients, the method comprising the acts of:

receiving a cellular phone call from a client;

identifying a client geographic location of the phone call;

comparing the client geographic location with a database;

correlating addresses with geographic locations and calculating the distance between the client geographical location and at least one geographical location listed in the database; and selecting, from among the geographic locations included in the database, the geographic location correlated with the client geographic location.

2. The method of claim 1, further comprising:

identifying the address correlated to the selected geographic location.

3. The method of claim 1, further comprising the act of:

identifying the client making the phone call.

4. The method of claim 3, wherein the act of identifying the client further comprises:

receiving, from the client, a client identifier resulting from a unique physiological characteristic of the client;

comparing the client identifier with a client database correlating clients with their physiological characteristics; and selecting which of the physiological characteristics corresponding to the client identifier to identify the client.

5. The method of claim 1, wherein the identifying act further comprises:

determining the geographic location of at least three cells which are monitoring the phone call;

applying a triangulation calculation to the determined ranges and geographic locations to determine the client geographic location.

6. The method of claim 1, wherein the identifying act further comprises:

determining the cell geographic location of at least one cell monitoring the phone call;

determining the range of the client from the at least one cell; and determining the orientation of the client relative to the at least one cell and calculating the client geographic location from the cell geographic location, the range and the orientation.

7. The method of claim 1, where the selecting act further comprises:

identifying the geographic location listed in the database which is least far from the client geographic location.

8. The method of claim 1, further comprising the act of:

identifying the time of the phone call.

9. The method of claim 1, further comprising the act of:

identifying whether the client is arriving at or departing from the location where the phone call is placed.

* * * * *